United States Patent [19]

Harris et al.

[11] Patent Number: 4,636,571
[45] Date of Patent: Jan. 13, 1987

[54] 4-CARBALKOXY-2-ETHYL-2,3-DIHYDROFURANS

[75] Inventors: Eugene G. Harris, West Chester; Richard G. Fayter, Jr., Fairfield, both of Ohio

[73] Assignee: National Distillers and Chemical Corporation, New York, N.Y.

[21] Appl. No.: 726,220

[22] Filed: Apr. 23, 1985

Related U.S. Application Data

[63] Continuation-in-part of Ser. No. 503,974, Jun. 13, 1983, Pat. No. 4,515,978.

[51] Int. Cl.$^4$ ............................................. C07D 307/02
[52] U.S. Cl. .................................. 549/484; 252/522 R
[58] Field of Search ...................... 549/484; 252/522 R

[56] References Cited

PUBLICATIONS

Jackson et al., "Chem. Abs.", vol. 94, (1984), 121,201r.

*Primary Examiner*—Anton H. Sutto
*Attorney, Agent, or Firm*—Kenneth D. Tremain; Gerald A. Baracka

[57] ABSTRACT

2,3-Dihydrofurans having highly desirable odor characteristics closely mimicking that of natural products are provided herein. The 2,3-dihydrofurans correspond to the formula

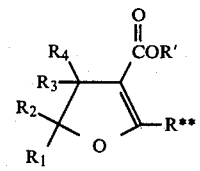

wherein R' is an alkyl group having from 1 to 4 carbon atoms, R** is an alkyl group having from 1 to 5 carbon atoms, $R_1$ is an alkyl group having from 1 to 4 carbon atoms, $R_2$ is hydrogen or an alkyl group having from 1 to 6 carbon atoms, and $R_3$ and $R_4$ are hydrogen or a methyl group. The 2,3-dihydrofuran compounds are useful in the preparation of fragrance compositions and fragranced articles and can be employed in conjunction with known fragrance materials to augment or enhance the aromas thereof.

8 Claims, No Drawings 4,636,571

4-CARBALKOXY-2-ETHYL-2,3-DIHYDROFURANS

CROSS REFERENCE TO RELATED APPLICATIONS

This is a continuation-in-part of copending application Ser. No. 503,974, filed June 13, 1983, now U.S. Pat. No. 4,515,978.

BACKGROUND OF THE INVENTION

1. Field of the Invention

This invention relates to dihydrofuran derivatives and, more specifically, to certain substituted-2,3-dihydrofurans which are useful fragrance compounds.

2. Description of the Prior Art

The use of synthetic fragrance chemicals has added a new dimension to the art of perfumery. As a result of the development of new synthetic perfume chemicals, perfumers have greater flexibility in developing fragrance formulations and are better able to mimic natural aromas. However, as perfumers become more adept in the use of synthetic materials for the formulation of sophisticated fragrances and developing the subtle nuances typically associated with natural fragrances, there is a growing demand for new synthetic fragrance compounds.

Furan derivatives are known to have desirable fragrance and flavor qualities. For example, ethyl furoate, n-amyl furoate, ethyl furyl beta-hydroxypropionate and furfural are reported as being useful for the formulation of perfumes, cosmetics and soaps. Furfuryl alkyl and aryl ethers are disclosed as flavor enhancers in U.S. Pat. No. 3,940,502.

Tetrahydrofurans are also disclosed to be useful for fragrance applications. U.S. Pat. No. 3,668,134, for example, discloses the use of esters/ethers of tetrahydrofurans as perfumery ingredients for detergent compositions. 3-Oximino-4-oxo-2,5-dimethyltetrahydrofuran is described in U.S. Pat. No. 4,116,982 and disclosed to have a fine caramel-like fragrance making it useful for the manufacture of scents and flavors. 2-Acetonyl-3,5-dimethyl-5-isopropyltetrahydrofuran is disclosed in U.S. Pat. No. 3,470,209 as having a pleasant spicy odor reminiscent of bay and eucalyptus. 2-(1'-Hydroxymethyl-ethyl)-5-methyl-5-vinyltetrahydrofuran is disclosed in U.S. Pat. No. 3,764,567 to be a useful for floral perfumes. In U.S. Pat. No. 3,227,731 carbonates of 1-(alpha-furyl)-2,2-dialkyl-1,3-dihydroxypropanes and 1-(alpha-tetrahydrofuryl)-2,2-dialkyl-1,3-dihydroxypropanes are indicated to be useful in perfume compounding.

2,3-Dihydrofurans having a vinyl group at the 2-position, a lower carboxylate radical at the 4-position and a methyl group at the 5-position have been reported in *Chemical Abstracts*, Volume 75, 87758y (1971): Volume 93, 71095r (1980): Volume 93, 239112v (1980): and Volume 94, 15458v (1981). Dihydrofurans of the same general type are also reported by Vinogradov et. al. in *Izv. Akad. Nauk SSSR Ser. Khimm,* 1981, (9), 2077–84 and Morlyan et. al. in Russian Patent (Inventor's Certificate) No. 979,346. The compounds of Vinogradov et. al. and Morlyan et. al. are obtained by the oxidative addition of 1,3-dicarbonyl compounds with dienes in acetic acid and in the presence of manganese (III) acetate and copper (II) acetate. Employing a similar reaction procedure, Heiba et. al. (*J. Chem Vol.,* Vol. 39, No. 23, 1974) have prepared and reported 2,3-dihydrofurans having a phenyl group substituted at the 2-position.

SUMMARY OF THE INVENTION

It is an object of this invention to provide novel dihydrofuran derivatives useful as fragrance derivatives. Another object is to provide novel dihydrofuran fragrance compounds which can be readily and economically prepared and which exhibit good stability and diffusivity. Yet another object is to provide 2,3-dihydrofuran derivatives having a more natural aroma.

These and other objects are realized by providing herein novel 2,3-dihydrofurans having at least one hydrocarbyl group, preferably alkyl, substituted at the 2-position on the ring, a carboxylate (carboalkoxy) group substituted at the 4-position on the ring, and a hydrocarbyl group, preferably alkyl, substituted at the 5-position on the ring. A second alkyl moiety may also be substituted at the 2-position and one or two alkyl groups may also be present at the 3-position.

One group of useful 2,3-dihydrofurans corresponding to the above general definition have the formula

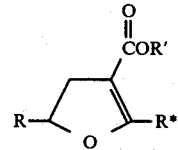

where R is an alkyl or vinyl group, R' is a $C_{1-4}$ alkyl group and R* is a hydrocarbon radical having from 1 to 10 carbon atoms. Novel compounds of this type include those wherein R is vinyl, R' is a $C_{1-4}$ alkyl and R* is a $C_{3-8}$ alkyl or alkenyl group.

A second preferred group of useful 2,3-dihydrofurans within the above general definition which can contain additional substituents on the 2- and 3-ring positions have the general formula

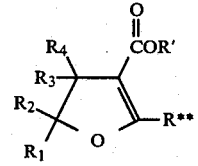

where R' is the same as defined above, R is a $C_{1-5}$ alkyl group, $R_1$ is a $C_{1-4}$ alkyl group, $R_2$ is hydrogen or a $C_{1-6}$ alkyl group, and $R_3$ and $R_4$ are hydrogen or methyl. These compounds have been found to have highly desirable odor characteristics closely mimicking that of natural products and they also have other advantages. It is even more advantageous if the total number of carbon atoms i n the alkyl substitutents, i.e., $R_1+R_2+R_3+R_4+R'+R$, does not exceed 10 and if the total number of carbon atoms of the alkyl group(s) substituted in the 2-position, i.e., $R_1+R_2$, does not exceed 6. Compounds wherein R' is methyl or ethyl, R** is methyl, $R_1$ is ethyl, $R_2$ is hydrogen or a $C_{1-4}$ alkyl, and $R_3$ and $R_4$ are hydrogen, are especially useful and form a particularly preferred embodiment of the invention.

DETAILED DESCRIPTION OF THE INVENTION

The novel 2,3-dihydrofurans of the present invention useful as fragrance compounds in a variety of fragrance applications necessarily have at least one hydrocarbyl group substituted at the 2-position on the ring, a carboxylate (carboalkoxy) moiety substituted at the 4-position, and a hydrocarbyl group substituted at the 5-position. For the purpose of this invention, the ring positions of the dihydrofuran are numbered as follows:

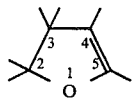

Two hydrocarbyl groups may be present at the 2-position. Additionally, one or two hydrocarbyl groups may be substituted at the 3-position. Particularly useful fragrance compounds having odor characteristics which closely mimic that of natural products and having other advantages are obtained when the hydrocarbyl substituents are saturated aliphatic, i.e., alkyl, groups.

2,3-Dihydrofurans of the invention correspond to the general formula

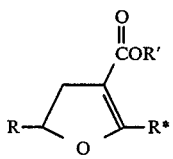

wherein R is an alkyl or vinyl group, R' is an alkyl group having from 1 to 4 carbon atoms, and R* is a hydrocarbyl radical having from 1 to 10 carbon atoms. R' can be a straight-chain or branched radical such as methyl, ethyl, n-propyl, iso-propyl, n-butyl, tert-butyl and sec-butyl. The hydrocarbon radical R* can be an aliphatic, cycloaliphatic or aromatic group. When R* is an aliphatic radical it can be straight-chain or branched and may be saturated or contain unsaturation. Useful cycloaliphatic radicals from which R* is selected will have from 3 to 6 carbon atoms in the ring and may be saturated or unsaturated. Especially useful cycloaliphatic radicals are cyclopentyl, cyclohexyl, cyclopentenyl, cyclohexenyl, cyclopentadienyl and cyclohexadienyl, which can also have one or more alkyl groups substitued thereon. Useful aromatic groups from which R* is 15 selected include phenyl, benzyl and $C_{1-4}$ alkyl- or $C_{1-4}$ alkoxy-substituted phenyl or benzyl. Novel 2,3-dihydrofurans of the above type are those wherein R is vinyl, R' is $C_{1-4}$ alkyl, and R* is $C_{3-8}$ alkyl or alkenyl and include:

4-carbomethoxy-5-methyl-2-vinyl-2,3-dihydrofuran;
4-carbethoxy-5-methyl-2-vinyl-2,3-dihydrofuran;
4-carbomethoxy-5-ethyl-2-vinyl-2,3-dihydrofuran;
4-carbomethoxy-5-n-pentyl-2-vinyl-2,3-dihydrofuran;
4-carbethoxy-5-n-pentyl-2-vinyl-2,3-dihydrofuran;
4-carbethoxy-5-n-pentenyl-2-vinyl-2,3-dihydrofuran;
4-carbethoxy-5-(3-methylbutyl)-2-vinyl-2,3-dihydrofuran;
4-carbethoxy-5-(4-methyl-3-pentenyl)-2-vinyl-2,3-dihydrofuran;
4-carbomethoxy-5-phenyl-2-vinyl-2,3-dihydrofuran;
4-carbethoxy-5-phenyl-2-vinyl-2,3-dihydrofuran;
5-benzyl-4-carbomethoxy-2-vinyl-2,3-dihydrofuran;
5-benzyl-4-carbethoxy-2-vinyl-2,3-dihydrofuran;
4-carbethoxy-5-(p-tolyl)-2-vinyl-2,3-dihydrofuran;
4-carbethoxy-5-(p-methoxyphenyl)-2-vinyl-2,3-dihydrofuran;
4-carboisopropoxy-5-isopropyl-2-vinyl-2,3-dihydrofuran;
4-carboisopropoxy-5-isopentenyl-2-vinyl-2,3-dihydrofuran;
and the like.

Highly useful 2,3-dihydrofuran fragrance compounds are obtained when all of the hydrocarbyl substituents on the ring are saturated aliphatic moieties. These compounds have the formula

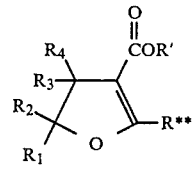

where R' is the same as defined above, i.e., a $C_{1-4}$ alkyl group, R is a $C_{1-5}$ alkyl group, $R_1$ is a $C_{1-4}$ alkyl group, $R_2$ is hydrogen or a $C_{1-6}$ alkyl group and $R_3$ and $R_4$ are hydrogen or methyl. Compounds corresponding to the above formula have odor characteristics which closely mimic that of natural products and also possess other advantages. Particularly useful fragrance compounds are obtained if the total number of carbon atoms in the alkyl substituents, i.e., $R_1+R_2+R_3+R_4+R'+R^{}$, does not exceed 10 and if the total number of carbon atoms in the alkyl group(s) present at the 2-position, i.e., $R_1+R_2$, does not exceed 6. Representative compounds of the above type include:

4-carbomethoxy-2-ethyl-5-methyl-2,3-dihydrofuran;
4-carbethoxy-2-ethyl-5-methyl-2,3-dihydrofuran;
4-carbopropoxy-2-ethyl-5-methyl-2,3-dihydrofuran;
4-carboisopropoxy-2-ethyl-5-methyl-2,3-dihydrofuran;
4-carbobutoxy-2-ethyl-5-methyl-2,3-dihydrofuran;
4-carbomethoxy-2-ethyl-5-ethyl-2,3-dihydrofuran;
4-carbethoxy-2-ethyl-5-ethyl-2,3-dihydrofuran;
4-carbomethoxy-2-ethyl-5-pentyl-2,3-dihydrofuran;
4-carbethoxy-2-ethyl-5-pentyl-2,3-dihydrofuran;
4-carbomethoxy-2-ethyl-5-(3-methylbutyl)-2,3-dihydrofuran;
4-carbethoxy-2-ethyl-5-(3-methylbutyl)-2,3-dihydrofuran;
4-carbomethoxy-2-ethyl-5-(4-methyl-3-pentyl)-2,3-dihydrofuran;
4-carbethoxy-2-ethyl-5-(4-methyl-3-pentyl)-2,3-dihydrofuran;
4-carbethoxy-2-ethyl-5-isopropyl-2,3-dihydrofuran;
4-carboisopropoxy-2-ethyl-5-isopropyl-2,3-dihydrofuran;
4-carboisopropoxy-2-ethyl-5-isopropyl-2,3-dihydrofuran;
4-carbomethoxy-2,5-dimethyl-2-ethyl-2,3-dihydrofuran;
4-carbethoxy-2,5-dimethyl-2-ethyl-2,3-dihydrofuran;
4-carbomethoxy-2,2,5-trimethyl-2,3-dihydrofuran;
4-carbethoxy-2,2,5-trimethyl-2,3-dihydrofuran;
4-carbethoxy-5-methyl-2-butyl-2,3-dihydrofuran;
4-carbethoxy-5-methyl-2-propyl-2,3-dihydrofuran;
4-carbomethoxy-2-isobutyl-3,3,5-trimethyl-2,3-dihydrofuran;
4-carbethoxy-2-isobutyl-3,3,5-trimethyl-2,3-dihydrofuran;
4-carbomethoxy-2-ethyl-2-isobutyl-3,3,5-trimethyl-2,3-dihydrofuran;
4-carbethoxy-2-ethyl-2-isobutyl-3,3,5-trimethyl-2,3-dihydrofuran;

4-carbethoxy-2-ethyl-2,3,3,5-tetramethyl-2,3-dihydrofuran;

and the like. Compounds wherein R' is methyl or ethyl, R** is methyl, $R_1$ is ethyl, $R_2$ is hydrogen or an alkyl group having from 1 to 4 carbon atoms, and $R_3$ and $R_4$ are hydrogen are especially useful and are a preferred embodiment of the invention.

In general, 2,3-dihydrofurans of the above types generally have pleasing natural fragrances. Depending on the number, type, and position of the ring substituents it is possible to obtain compounds which are reminiscent of a variety of natural products. For example, the 2,3-dihydrofurans can have floral, woody, herbaceous, green, nutty, fruity, or vegetable aromas and, most typically, several of these notes 25 will be present even though one note may be predominant. While the various individual fragrance notes may vary in intensity, the products of this invention exhibit good overall intensity without being overwhelming and also exhibit good diffusivity, stability, and dryout characteristics.

The 2,3-dihydrofurans are useful for the preparation and formulation of fragranced products, such as perfumes, colognes, shampoos, deodorants, shaving creams and gels, body lotions and creams, detergent and bar soaps, and the like. The amount of 2,3-dihydrofuran compound employed depends on the particular formulation and, to some extent, whether the 2,3-dihydrofuran is the sole fragrance material used or if it is used in conjunction with other fragrance materials. In general, the amount of 2,3-dihydrofuran present in the formulation can vary from trace amounts to about 50 percent by weight of the formulation. More usually, however, the 2,3-dihydrofuran constitutes from about 0.01 to 10 weight percent of the finished formulation.

The 2,3-dihydrofuran fragrance derivatives having R'=methyl or ethyl, R**=methyl, $R_1$=ethyl, $R_3$=$C_{1-4}$ alkyl, and $R_3$=$R_4$=hydrogen are especially advantageous since they have very desirable floral odors, most notably jasmonic and chamomile in character, which closely mimic and are reminiscent of the natural floral products. Additionally, it has been observed that these products do not induce contact sensitization or elicit an allergic response in the standard skin sensitization potential test (Repeated Insult Patch Test). This latter result is unexpected in view of the sensitization potential exhibited by closely related 2,3-dihydrofuran compounds wherein all of the hydrocarbon ring substituents are not saturated aliphatic moieties.

The novel 2,3-dihydrofuran derivatives of the present invention can be obtained by isomerization of the corresponding cyclopropyl ketone derivative in accordance with the following general equation:

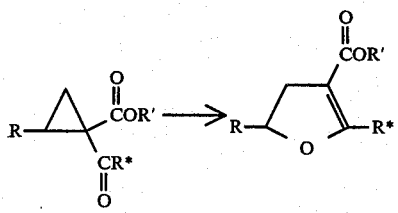

wherein R, R' and R* are the same as previously defined. The isomerization process is fully described in U.S. Pat. No. 4,487,946 details of which are incorporated herein by reference thereto. The isomerization is typically carried out at a temperature from 60° C. to 200° C. utilizing from about 0.5 to 20 weight percent, based on the cyclopropyl ketone, of an onium catalyst. Most generally, the onium catalyst is present in an amount from 2 to 15 weight percent and is a quaternary ammonium or phosphonium compound containing at least six carbon atoms and corresponding to the formula

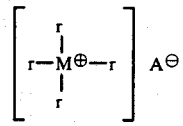

where M is nitrogen or phosphorous, r represents a hydrocarbon radical having from 1 to 22 carbon atoms, and A is chloride or bromide. Particularly useful onium catalysts for the isomeriztion process contain at least 10 carbon atoms and include tetrabutylammonium chloride; tetrabutylammonium bromide; dimethyldibenzylammonium chloride; dimethyldibenzylammonium bromide; trimethylbenzylammonium chloride; trimethylbenzylammonium bromide; tricaprylylmethylammonium chloride; tricaprylylmethylammonium bromide; tributylhexadecylphosphonium chloride; tributylhexadecylphosphonium bromide; and the like.

Preferably, the isomerization reaction is carried out in the absence of a diluent or solvent and the cyclopropyl ketone is essentially free of water, caustic or salts. If a solvent or diluent is employed, it must be inert to the reaction conditions and must be separated from the 2,3-dihydrofuran at the conclusion of the reaction by distillation or the like. The onium catalyst is also removed from the 2,3-dihydrofuran by distillation. In order to obtain the preferred fragrance derivatives, the resulting 2,3-dihydrofuran obtained from the isomerization procedure is hydrogenated to reduce the olefinic unsaturation in the ring substituents but not the unsaturation in the ring. Known hydrogenation procedures are employed for this purpose.

Useful 2,3-dihydrofurans are also obtained from the oxidative 1,2-addition of 1,3-dicarbonyl compounds to conjugated dienes in accordance with the procedure described by Vinogradov et. al. in *Izv. Akad. Nauk SSR, Ser. Khimm*, 1981, (9), 2077–84. This reaction is represented by the equation

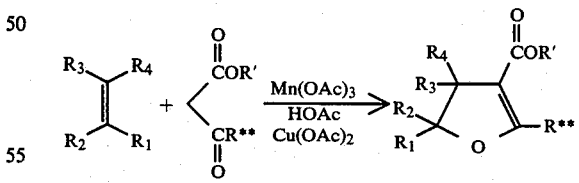

where $R_1$, $R_2$, $R_3$, $R_4$, R' and R** are the same as previously defined. The reaction is generally carried out in acetic acid containing manganese (III) and a catalytic amount of copper (II). Acetoacetic ester and 1,3-butadiene, isoprene, or piperylene are commonly employed reactants for this type of reaction. The 2,3-dihydrofuran is distilled to remove manganese and copper residues and then hydrogenated to reduce olefinic unsaturation present in the hydrocarbon substituents. Conventional hydrogenation procedures which do not reduce the ring unsaturation are employed for this purpose.

The following examples illustrate the invention more fully. In the examples, all parts and percentages are on a weight basis unless otherwise indicated.

EXAMPLE I

In accordance with the phase transfer procedure of U.S. Pat. No. 4,252,739, ethyl 1-hexanoyl-2-vinylcyclopropane-1-carboxylate was prepared by the reaction of 0.53 mole ethyl hexanoyl acetate ($CH_3(CH_2)_4COCH_2COOC_2H_5$) 0.66 mole 1,4-dichlorobutene-2, and 1.06 moles potassium hydroxide. The reaction was carried out in a mixture of water and methylene chloride utilizing 0.0133 mole tricaprylylmethylammonium chloride as the phase transfer catalyst. The resulting reaction product was then filtered through a sintered glass funnel to remove excess potassium hydroxide and insoluble salts formed during the reaction and neutralized with 10 percent sulfuric acid. The crude product obtained after drying and removal of the methylene chloride contained approximately 95 percent ethyl 1-hexanoyl-2-vinylcyclopropane-1-carboxylate.

The ethyl 1-hexanoyl-2-vinylcyclopropane-1-carboxylate obtained above (120 grams) was combined with 25.6 grams tricaprylylmethylammonium chloride and heated at 110° C. under a nitrogen atmosphere with agitation to isomerize the cyclopropyl ketone to the corresponding 2,3-dihydrofuran. After three hours, gas chromatographic analysis showed the reaction mixture to contain 41 percent of the desired product 4-carbethoxy-5-pentyl-2-vinyl-2,3-dihydrofuran. Heating was continued at 110° C. until the 4-carbethoxy-5-pentyl-2-vinyl-2,3-dihydrofuran content was increased to 87 percent. Upon distillation of the reaction product essentially pure 4-carbethoxy-5-pentyl-2-vinyl-2,3-dihydrofuran was obtained. The 4-carbethoxy-5-pentyl-2-vinyl-2,3-dihydrofuran was a clear, colorless liquid (B.P. 103°-109° C. @ 2 mm Hg; $n_D^{25°} 1.4709$) and had a sweet lactonic note useful in lavender or bergamot areas.

The structure of the product

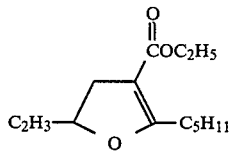

was confirmed by infrared and nuclear magnetic resonance spectroscopy.

IR (film): 2960, 2930, 2870, 1695, 1637, 1370, 1252, 1225, 1173, 1104, 1050, 970 and 767 cm$^{-1}$.

nmr(CDCl$_3$)δ: 0.90 (t, 3H (CH$_3$—CH$_2$—CH$_2$—)), 1.28 (t, 3H (CH$_3$—CH$_2$—O—CO)), 1.45 (m, 6 methylene H), 2.70 (br.t., 2 methylene H adj. to ring), 3.03 (m, 2 ring methylene H), 4.23 (q, 2H (CH$_3$—CH$_2$—O—CO—)), 5.18 (m, 3 vinyl H), 6.02 (m, 1 ring H).

EXAMPLE II

4-Carbethoxy-5-pentyl-2-vinyl-2,3-dihydrofuran prepared in accordance with the procedure of Example I was hydrogenated to obtain 4-carbethoxy-2-ethyl-5-pentyl-2,3-dihydrofuran. For the reaction, 13 grams of the 4-carbethoxy-5-pentyl-2-vinyl-2,3-dihydrofuran and 75 mls ethyl acetate were charged to the reactor of a Parr apparatus. The system was thoroughly purged with nitrogen and 0.65 gram of a hydrogenation catalyst (5 percent palladium on carbon) was added under a nitrogen atmosphere. After additional nitrogen purging, shaking was begun and the system was pressurized with hydrogen to 15 psig. The system was repressurized as necesary until no futher hydrogen uptake was noted. The reaction mixture was then filtered through Dicalite to remove the catalyst. Ethyl acetate was removed under reduced pressure. Gas chromatographic analysis indicated 98 percent yield crude 4-carbethoxy-2-ethyl-5-pentyl-2,3-dihydrofuran. The crude product was fractionated using a spinning-band distillation apparatus to obtain essentially pure 4-carbethoxy-2-ethyl-5-pentyl-2,3-dihydrofuran (B.P. 112°-114° C. @ 1 mm Hg. $n_D^{25°} 1.4636$). The structure

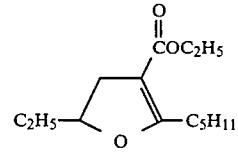

was confirmed by infrared and nuclear magnetic resonance spectroscopy.

IR (film): 2970, 2930, 2870, 1694, 1636, 1462, 1370, 1330, 1255, 1228, 1173, 1104, 1048, 973 and 765 cm$^{-1}$.

nmr (CDCl$_3$)δ: 1.28 (m, 14H (—CH$_2$—CH$_2$ and CH$_3$—CH2—type hydrogens)), 1.29 (t, 3H (CH$_3$—CH$_2$—O—CO—)), 2.68 (br.t., 2 methylene H adj. to ring), 2.86 (m, 2 ring methylene H), 4.19 (q, 2H (CH$_3$—CH$_2$—O—CO)), 4.63 (m, 1 ring H).

The 4-carbethoxy-2-ethyl-5-pentyl-2,3-dihydrofuran had very pleasant notes compatible with and suitable for blending in Jasmone and citrus fragrance compositions. The product had a more natural and smoother odor profile than the unhydrogenated starting material.

EXAMPLE III

In a manner similar to that described in Example I, 4-carbethoxy-5-(3-methylbutyl)-2-vinyl-2,3-dihydrofuran was prepared by the isomerization of ethyl 1-(4-methylpentanoyl)-2-vinylcyclopropane-1-carboxylate.

For the reaction, 125 mls of the ethyl 1-(4-methylpentanoyl)2-vinylcyclopropane-1-carboxylate was combined with 25.4 grams tricaprylylmethylammonium chloride. The mixture was stirred at 100° C. for approximately eleven hours, after which time gas chromatographic analysis showed the reaction mixture to contain about 85 percent 4-carbethoxy-5-(3-methylbutyl)-2-vinyl-2,3-dihydrofuran. Heating was terminated and the crude product distilled using a spinning-band distillation apparatus fitted with a 12 inch column. Essentially pure 4-carbethoxy-5-(3-methylbutyl)-2-vinyl-2,3-dihydrofuran was obtained (B.P. 101°-102° C. @ 1 mm Hg; $n_D^{25°} 1.4742$). The 4-carbethoxy-5-(3-methylbutyl)-2-vinyl-2,3-dihydrofuran had a pleasing fragrance with a slightly weedy, fatty, nutty-scotch whiskey odor profile. The structure of the product

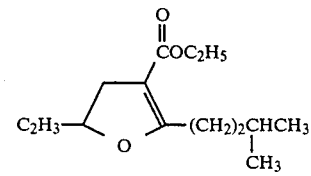

was confirmed by infrared nuclear magnetic resonance spectroscopic analysis.

IR (film): 2959, 2930, 2875, 1699, 1636, 1369, 1311, 1250, 1234, 1192, 1172, 1135, 1107, 1054, 970 and 765 cm$^{-1}$.

nmr(CDCl$_3$) δ: 0.90 (d, 6H ((C$\underline{H}_3$)$_2$—CH)), 1.27 (t, 3H (C$\underline{H}_3$—CH$_2$—O—CO—)), 1.52 (m, 3H (—CH$_2$—C$\underline{H}_2$—CH—)), 2.68 (br.t, 2H (2 methylene H adj. to ring)), 2.90 (m, 2 ring methylene H), 4.23 (q, 2H (CH$_3$—C$\underline{H}_2$—O—CO—)), 5.23 (m, 3 vinyl H), 6.09 (m, 1 ring H).

EXAMPLE IV

4-Carbethoxy-5-(3-methylbutyl)-2-vinyl-2,3-dihydrofuran prepared in accordance with Example III was hydrogenated to obtain 4-carbethoxy-2-ethyl-5-(3-methylbutyl)-2,3-dihydrofuran. The hydrogenation procedure employed was the same as described in Example II. After removal of the catalyst and ethyl acetate, 17.47 grams crude 4-carbethoxy-2-ethyl-5-(3-methylbutyl)-2,3-dihydrofuran was obtained. Distillation of the crude product yielded essentially pure 4-carbethoxy-2-ethyl-5-(3-methylbutyl)-2,3-dihydrofuran boiling at 102° C.–103° C. at 0.6 mm Hg (n$_D^{25°}$1.45211). The material had an intense very natural fruity odor - strawberry and apple predominating, with traces of chamomile. Even though the odor characteristics of the hydrogenated product were quite intense, the overall impact was more natural and less "chemical" than that of the unhydrogenated precursor. The structure of the

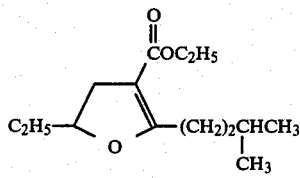

was confirmed by infrared and nuclear magnetic resonance spectroscopy.

IR (film): 2980, 2955, 2900, 1705, 1640, 1472, 1375, 1340, 1265, 1240, 1175, 1145, 1110, 1055, 970 and 770 cm$^{-1}$.

nmr(CDCl$_3$)δ: 0.93 (d, 6H (C$\underline{H}_3$)$_2$—CH—)), 1.28 (t, 3H (C$\underline{H}_3$—CH$_2$—O—CO—)), 1.29 (m(complex), 8H), 2.68 (br.t, 2H (2 methylene H adj. to ring)), 2.79 (m, 2 ring methylene H), 4.21 (q, 2H (CH$_3$—C$\underline{H}_2$—O—CO)), 4.65 (m, 1 ring H).

EXAMPLE V

In a manner similar to that previously described in Example I, ethyl 1-(5-methyl-4-hexenoyl)-2-vinylcyclopropane-1-carboxylate, obtained by the condensation of ethyl 5-methyl-4-hexenoylacetate and 1,4-dichlorobutene-2 under phase transfer conditions, was isomerized to obtain 4-carbethoxy-5-(4-methyl-3-pentenyl)-2-vinyl-2,3-dihydrofuran. The isomeriztion was carried out at 110° C. under a nitrogen atmosphere using 19.6 weight percent tricaprylylmethylammonium chloride catalyst. After about three hours, chromatographic analysis confirmed the reaction mixture to contain 92 percent crude 4-carbethoxy-5-(4-methyl-3-pentenyl)-2-vinyl-2,3-dihydrofuran. Distillation of the isomerized product afforded 15 grams pure 4-carbethoxy-5-(4-methyl-3-pentenyl)-2-vinyl-2,3-dihydrofuran (B.P. 104°–110° C. @ 0.6 mm Hg: n$_D^{25°}$1.4910). The clear, colorless liquid had a somewhat hedge-like aroma with nuances of chamomile. The structure of the product

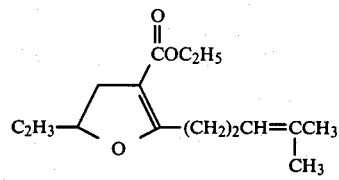

was confirmed by the nuclear magnetic resonance and infrared spectral data.

IR (film): 2975, 2920, 2875, 1691, 1633, 1447, 1372, 1310, 1232, 1155, 1107, 1065, 1025, 972, 915 and 765 cm$^{-1}$.

nmr(CDCl$_3$) δ: 1.30 (t, 3H (C$\underline{H}_3$—CH$_2$—O—CO)), 1.68 (d, 6H (C$\underline{H}_3$)$_2$=CH—)), 2.42 (br.t, 2H (—CH$_2$—CH=C(CH$_3$)$_2$)), 2.75 (br.t, 2H (2 methylene H adj. to ring)), 2.93 (m, 2 ring methylene H, part. hidden), 4.25 (q, 2H (CH$_3$—C$\underline{H}_2$—O'CO)), 5.23 (m, 4 vinyl H), 6.07 (m, 1 ring H).

EXAMPLE VI

The product of Example V was hydrogenated to obtain 4-carbethoxy-2-ethyl-5-(4-methyl-3-pentenyl)-2,3-dihydrofuran. Five percent by weight catalyst (5% Pd on a carbon support) was used. Hydrogenation was essentially complete in three hours. After removal of the catalyst and ethyl acetate solvent, the crude hydrogenated product was distilled using a 50-plate spinning-band distillation apparatus to obtain essentially pure 4-carbethoxy-2-ethyl-5-(4-methyl-3-pentenyl)-2,3-dihydrofuran. The product (B.P. 58° C. @ 0.01 mm Hg: n$_D^{25°}$1.4791) had a fruity chamomile-like character and was more natural, smoother, and less weedy in overall odor quality than the unsaturated precursor. The structure

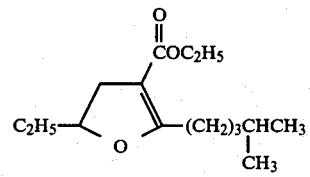

was confirmed by infrared and nuclear magnetic resonance spectroscopy.

IR (film): 2970, 2930, 2875, 1690, 1635, 1450, 1373, 1236, 1156, 1107, 1066, 1026, 985, 830 and 765 cm$^{-1}$.

nmr(CDCl$_3$)δ: 0.98 (t, 3H (C$\underline{H}_3$—CH$_2$—C—)),
1.28 (t, 3H (C$\underline{H}_3$—CH—O—CO—)),
1.52 (q, 2H (CH$_3$—C$\underline{H}_2$—C—)hidden),
1.68 (d, 6H ((CH$_3$)$_2$C=CH—)),
2.35 (br.t, 2H (—CH$_2$—CH=C(CH$_3$)$_2$)),
2.73 (br.t, 2H (2 methylene H adj. to ring)),
2.93 (m, 2 ring methylene H, part. hidden),
4.22 (q, 2H (CH$_3$—C$\underline{H}_2$—O—CO—)),
4.55 (m, 1 ring H),
5.23 (br.t, 1 vinyl H).

EXAMPLE VII

4-Carbethoxy-5-phenyl-2-vinyl-2,3-dihydrofuran was obtained in the usual manner by isomerizing ethyl 1-benzoyl-2-vinylcyclopropane-1-carboxylate. To catalyze the isomerization, tricaprylylmethylammonium chloride was employed at a 20 percent weight level.

The mixture was heated at 150° C. for about two hours after which time only about 7 percent of the cyclopropyl ketone remained. After two distillations, essentially pure 4-carbethoxy-5-phenyl-2-vinyl-2,3-dihydrofuran was obtained. The product (B.P. 110° C. @ 0.1 mm Hg: $n_D^{25°}1.5570$) had a pleasing aroma that was somewhat coumarin-like in odor character. Nuclear magnetic resonance and infrared spectroscopic analysis confirmed the structure

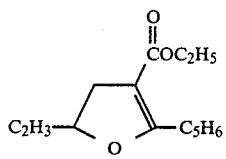

IR (film) 2980, 1697, 1622, 1598, 1496, 1446, 1370, 1240, 1085, 1070, 987, 926, 760 and 695 cm$^{-1}$.

nmr(CDCl$_3$) δ: 1.20 (t, 3H (C$\underline{H_3}$—CH$_2$—O—CO—)), 3.15 (oct, 2 ring methylene $\underline{H}$), 4.17 (q, 2H (CH$_3$—C$\underline{H}_2$—O—CO—)), 4.27 (m, 3 vinyl H), 6.13 (m, 1 ring $\underline{H}$), 7.73 (m, 5 phenyl H).

EXAMPLE VIII

4-Carbethoxy-5-methyl-2-vinyl-2,3-dihydrofuran was prepared in accordance with the oxidative addition procedure described by Vinogradov et. al. in *Izv. Akad Nauk SSR, Ser. Khimm*, 1981, (9), 2088–84. For the reaction, 98 grams manganous acetate tetrahydrate was combined with 300 mls acetic acid in a glass reaction vessel. The mixture was heated to 60° C. with stirring and 15.8 grams potassium permanganate slowly added. The temperature was maintained below 70° C. during the addition and, when the addition was complete, the mixture was stirred for thirty minutes and then cooled to approximately 20° C. Two grams cupric acetate and 180 grams ethyl acetoacetate were then charged to the reactor and, after the mixture was stirred for five minutes, butadiene was slowly bubbled into the mixture which was maintained at 25° C. After thirty grams butadiene was added, the mixture was stirred for five minutes at 30° C. and then heated at 60° C. for fifteen minutes. At this point, the color of the reaction mixture changed from pink to brown (indicating reduction of Mn (III) to Mn (II)) and essentially all of the starting ethyl acetoacetate was determined by gas chromatographic analysis to be reacted. The mixture was cooled and filtered to remove insoluble salts. The salts were washed twice with acetic acid (50 mls) and the combined filtrates stripped on a rotary evaporator at 90° C. and reduced pressure to remove the acetic acid. The resulting residue was poured into 250 mls water and extracted three times with n-hexane (75 mls). The combined organic extracts were then washed with aqueous sodium bicarbonate, dried over sodium sulfate, and stripped on a rotary evaporator under reduced pressure to remove the organic solvent. The crude product was vacuum distilled to obtain a 65% yield of essentially pure (99%) 4-carbethoxy-5-methyl-2-vinyl-2,3-dihydrofuran (B.P. 108–110 @ 10 mm Hg).

EXAMPLE IX

One hundred seventy-five grams 5-carbethoxy-5-methyl-2-vinyl-2,3-dihydrofuran obtained by the procedure of Example VIII was combined with 1.75 grams hydrogenation catalyst (5% palladium on carbon) and hydrogenated following the procedure of Example II. Upon completion of the hydrogenation, the product was filtered to remove the catalyst and distilled through an adiabatic column fitted with a Perkin-Triangle head to obtain 96.6% pure 4-carbethoxy-2-ethyl-5-methyl-2,3-dihydrofuran in 91% yield (B.P. 106° C. @ 9.5mm Hg; $n_D^{25°}1.4670$).

The structure of the product

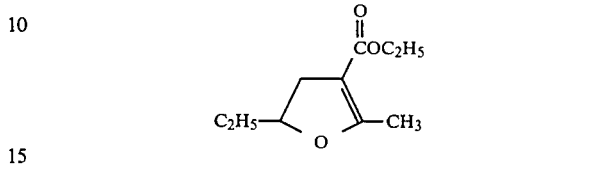

was confirmed by infrared and nuclear magnetic resonance spectroscopy.

I.R. (film): 2880–2980, 1700, 1645, 1230, 1080 cm$^{-1}$.

nmr (CDCl$_3$) δ: 1.00 (m, 3H (C—CH$_2$C$\underline{H_3}$)), 1.33 (t, 3H (C—CH$_2$C$\underline{H_3}$)), 1.70 (m, 2H (C—C$\underline{H_2}$—CH$_3$)), 2.25 (t, 3H (C(O)(=C)C$\underline{H_3}$)), 2.80 (m, 2H (ring methylene)), 4.26 (q, 2H (—O—C$\underline{H_2}$—CH$_3$)), 4.50 (m, 1H (ring H)), The 4-carbethoxy-2-ethyl-5-methyl-2,3-dihydrofuran had a very diffusive, herbaceous, natural, chamomile note with nuances of celery, lovage, and maltol. It is useful in formulating synthetic Roman chamomile oil and also gives good effects in other florals, such as lavender. The 4-carbethoxy-2-ethyl-5-methyl-2,3-dihydrofuran was much smoother, more natural, and less vegetable-like than the unhydrogenated vinyl precursor and was more suitable for use in floral perfume compositions.

The 4-carbethoxy-2-ethyl-5-methyl-2,3-dihydrofuran was added to a common herbal perfume base at a 1 weight percent level and imparted a desirable chamomile nuance to the overall odor character. Similarly, 10 weight percent 4-carbethoxy-2-ethyl-5-methyl-2,3-dihydrofuran was added to a perfume base designed as a chamomile oil replacement and imparted a more natural Roman chamomile-like odor character to the perfume base.

The 2,3-dihydrofuran derivative of this example was also blended into a cosmetic grade talc at a concentration of 0.5 weight percent. A portion of the fragranced talc was subjected to ultraviolet radiation for eight hours and no noticeable discoloration or change in the odor character was observed. Another portion of the fragranced talc was stored at 45° C. in a closed container for two weeks with no discoloration or change in the chamomile-like odor character of the product. In a similar manner, a fragranced detergent was prepared by adsorbing 0.1 weight percent of the 4-carbethoxy-2-ethyl-5-methyl-2,3-dihydrofuran on a commercially available unfragranced detergent. The resulting detergent had a pleasing fragrance similar to that of the 2,3-dihydrofuran fragrance compound. There was no noticeable change in odor or color of the fragranced detergent after storage for one year in a closed container.

To further demonstrate the utility of the 4-carbethoxy-2-ethyl-5-methyl-2,3-dihydrofuran, fragranced soap bars were prepared. For the preparation, 1,800 grams of a commercial nonscented soap stock obtained by the Mazzoni process was employed. Water was added as required during the processing to maintain the desired plasticity. The fragrance (1 percent by weight) was added and thoroughly blended before the soap stock was refined and extruded (plodded) in tubular form. Soap bars were then stamped from sections of the extruded tube. The fragranced bars had odor characteristics similar to that of the 4-carbethoxy-2-ethyl-5-methyl-2,3-dihydrofuran and exhibited good stability—no change in color or odor properties upon exposure to ultraviolet radiation for eight hours or after storage under ambient conditions for one year.

EXAMPLE X

In addition to the improved fragrance characteristics, the 4-carbethoxy-2-ethyl-5-methyl-2,3-dihydrofuran also proved to be much less likely to elicit an allergic response than the 4-carbethoxy-5-methyl-2-vinyl-2,3-dihydrofuran precursor. This was demonstrated using a conventional skin sensitization potential test (Repeated Insult Patch Test) in accordance with standard procedures. Both compounds were tested as 10 percent V/W solutions prepared in mineral oil. The study was carried out on 51 volunteers and all applications were by 24 hour contact occlusive patches. The test material was repeatedly applied to the same test site for a three-week period. No applications were then made for two weeks. At the end of the two-week period, a challenge (application) was made to a naive (new) test site. Strong irritation at the new test site indicates an allergic response. Compounds which give such a response are considered to be much less suitable for use as fragrance chemicals since, at the very least, they will have restrictions placed on their use. Under the conditions of this study, the 4-carbethoxy-5-methyl-2-vinyl-2,3-dihydrofuran was shown to induce contact sensitization in several of the test subjects whereas none of the subjects displayed any contact sensitization potential for the 4-carbethoxy-2-ethyl-5-methyl-2,3-dihydrofuran.

EXAMPLE XI

To demonstrate the ability to obtain 4-carbethoxy-2-ethyl-5-methyl-2,3-dihydrofuran by other procedures, the following experiment was conducted. For this reaction, manganous acetate tetrahydrate (98 grams), acetic acid (100 mls) and n-hexane (100 mls) were charged to a glass reactor and heated to reflux. Heating was terminated and potassium permanganate (15.8 grams) added. This mixture was refluxed for fifteen minutes, cooled to 20° C., and cupric acetate (2 grams) and ethyl acetoacetate (65 grams) added. At this point the mixture became very viscous and additional acetic acid (50 mls) and n-hexane (50 mls) were added. Butadiene (40 grams) was then bubbled into the mixture over a twenty minute period while maintaining the temperature below 24°. After refluxing for thirty minutes, the cooled mixture was extracted with n-hexane using a liquid-liquid extractor. The salts remaining in the extractor were dissolved in water and the resulting aqueous solution extracted with n-hexane. All of the hexane extracts were combined and the solvent removed under reduced pressure. The residue was charged to a hydrogenation apparatus with 50 mls hexane and 0.7 grams supported catalyst (5% Pd on carbon). The hydrogenation was carried out at 40 psig for 1½ hours. Work up of the product in the usual manner yielded essentially pure 4-carbethoxy-2-ethyl-2-methyl-2,3-dihydrofuran. While the yield of the product was somewhat less than that obtained in Examples VIII and IX, the chemical, physical and fragrance properties of the products were the same.

EXAMPLE XII

4-Carbethoxy-5-methyl-2-vinyl-2,3-dihydrofuran was prepared using a phase transfer procedure similar to that of Example I. For the reaction, three grams tricaprylylmethylammonium chloride, 62 grams potassium hydroxide, and 100 mls sulfolane were charged to a reactor and a mixture of 65 grams ethyl acetoacetate and 95 grams 1,4-dichlorobutene-2 slowly added over a period of one hour while maintaining the temperature below 30° C. The mixture was then stirred for two hours at ambient temperature and then heated to 150° C. until the reaction was essentially complete. The reaction mixture was poured into ice-water, extracted with ether, and the ether evaporated using a rotary evaporator. The resulting product, which consisted of essentially a 1:1 mixture of 4-carbethoxy-5-methyl-2-vinyl-2,3-dihydrofuran and ethyl-1-acetyl-2-vinylcyclopropane-1-carboxylate, was distilled. Sixty grams of the 4-carbethoxy-5-methyl-2-vinyl-2,3-dihydrofuran obtained from the distillation was combined with 100 mls ethyl acetate and 0.4 grams supported hydrogenation catalyst (5% Pd on carbon) and hydrogenated in the usual manner. The catalyst was removed at the conclusion of the hydrogenation by filtration and ethyl acetate stripped under reduced pressure to obtain crude 4-carbethoxy-2-ethyl-5-methyl-2,3-dihydrofuran. Distillation of the crude product yielded essentially pure 4-carbethoxy-2-ethyl-5-methyl-2,3-dihydrofuran with chemical and physical properties and fragrance characteristics the same as described for the product of Example IX.

EXAMPLE XIII

4-Carbethoxy-5-methyl-2-(4-methyl-3-pentenyl)-2-vinyl-2,3-dihydrofuran was obtained by the reaction of myrcene (68 grams) and ethyl acetoacetate (65 grams) in accordance with the oxidative addition procedure of Example VIII. For the reaction, manganese (III) acetate prepared from potassium permanganate (29 grams) and manganese (II) acetate tetrahydrate (40 grams) and dissolved in 300 mls acetic acid was employed. Cupric acetate (1 gram) was the catalyst. The 4-carbethoxy-5-methyl-2-(4-methyl-3-pentenyl)-2-vinyl-2,3-dihydrofuran was obtained in 70% yield and was hydrogenated in accordance with the general procedure of Example IX. The hydrogenation was carried out at 40 psig using 5% Pd on carbon catalyst. The resulting crude product was distilled to provide essentially pure 4-carbethoxy-2-ethyl-5-methyl-5-(4-methyl-3-pentenyl)-2,3-dihydrofuran (B.P. 60° C. @ 0.7 mm Hg: $n_D^{25°}$ 1.4794). The structure of the product

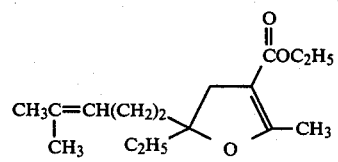

was confirmed by infrared and nuclear magnetic resonance spectroscopy.

I.R. (film): 2860–2960, 1690, 1635, 1240, 1065 cm$^{-1}$.

nmr (CDCl$_3$) δ: 0.88 (t, 3H (C—CH$_2$CH$_3$)), 1.25 (t, 3H (O—CH$_2$—CH$_3$)), 1.64 (d, 6H (C—CH$_2$—CH$_2$—CH=C(CH$_3$)$_2$)), 1.75 (m, 4H (C—CH$_2$—CH$_2$—CH=C(CH$_3$)$_2$)), 1.75 (m, 2H (C—CH$_2$—CH$_3$)), 2.17 (t, 3H (C(O)(=C)(CH$_3$)), 2.68 (m, 2H (ring methylene)),
4.21 (q, 2H (O—CH₂—CH₃)),
5.20 (m, 1H (C—CH₂—CH₂—CH═C(CH₃)₂)).

The product had a very natural fragrance reminiscent of sesquiterpene alcohols or sesquiterpene-like bisabolene, farnesene or nerolidol and was suitable for use in floral, jasmine, gardenia, and orange blossom formulations. The product also exhibited some woody character.

EXAMPLE XIV

Following the procedure of Example XII, 4-carbomethoxy-2-ethyl-5-methyl-2,3-dihydrofuran was obtained by the reaction of 1,4-dichlorobutene-2 (500 grams) and methyl acetoacetate (500 grams). Five hundred grams potassium hydroxide and 30 grams tricaprylylmethylammonium chloride were also employed for the reaction which was carried out in sulfolane. One hundred thirty grams crude 4-carbomethoxy-5-methyl-2-vinyl-2,3-dihydrofuran obtained from the reaction was hydrogenated at 40 psig using 1 weight percent supported catalyst (5% Pd on carbon). Two distillations of the crude product afforded 4-carbomethoxy-2-ethyl-5-methyl-2,3-dihydrofuran in 99.4 percent purity (B.P. 124°–126° C. @ 37 mm Hg; $n_D^{25°}$1.4708). The product had a very natural herbaceous odor making it suitable for lavender and chamomile formulations. The product also exhibited a very desirable safrole-like character which was not evident in the unhydrogenated precursor. The structure of the product

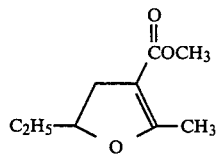

was confirmed by infrared and nuclear magnetic resonance spectroscopic analysis.

I.R. (film): 2860–2960, 1700, 1635, 1435, 1225, 1080 cm⁻¹.

nmr (CDCl₃)δ: 1.00 (t, 3H (C—CH₂—CH₃)), 1.70 (8, 2H (C—CH₂—CH₃)), 2.25 (t, 3H (C(O)(═C)(CH₃))), 2.75 (m, 2H (ring methylene)), 3.80 (s, 3H (—O—CH₃)), 4.68 (m, 1H (ring H)).

To demonstrate the ability to obtain fragranced soap bars having a highly desirable odor, 0.5 weight percent 4-carbomethoxy-2-ethyl-5-methyl-2,3-dihydrofuran was thoroughly blended into a molten cosmetic-grade tallow/coconut fatty soap stock. The mixture was poured into soap molds and allowed to cool and solidify. In addition to having a pleasing floral character, the fragranced bars exhibited good color and odor stability.

EXAMPLE XV

Utilizing the oxidative addition procedure detailed in the foregoing examples, isoprene (34 grams) and ethyl acetoacetate (65 grams) were reacted. The manganese (III) acetate was prepared from potassium permanganate (30 grams) and manganese (II) acetate tetrahydrate (196 grams) and was dissolved in 100 mls acetic anhydride and 200 mls acetic acid. Cupric acetate (1.8 grams) was the catalyst. The product obtained from the reaction consisted of a mixture of 4-carbethoxy-2,5-dimethyl-2-vinyl-2,3-dihydrofuran and 4-carbethoxy-2-isopropenyl-5-methyl-2,3-dihydrofuran present in a weight ratio of about 9:1.

A portion of the mixture was distilled to obtain 99+% pure 4-carbethoxy-2,5-dimethyl-2-vinyl-2,3-dihydrofuran (B.P. 91° C. @ 4 mm Hg; $n_D^{25°}$1.4756). The structure of the product

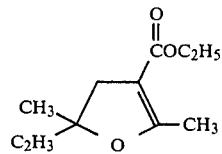

was confirmed by infrared and nuclear magnetic resonance spectroscopy.

I.R. (film): 3080, 2860–2960, 1695, 1630, 1235, 1060 cm⁻¹.

nmr (CDCl₃) δ: 1.22 (t, 3H (—O—CH₂CH₃)), 1.40 (s, 3H (—C(O)(C═C)(CH₃))), 2.17 (t, 3H (C(O)(═C)(CH₃))), 2.78 (m, 2H (ring methylene)), 4.17 (q, 2H (—O—CH₂CH₃)), 5.28 (m, 2H (CH₂═CH—)), 6.00 (m, 1H (CH₂═CH—)).

The remainder of the mixture of the 4-carbethoxy-2,5-dimethyl-2-vinyl-2,3-dihydrofuran and 4-carbethoxy-2-isopropenyl-5-methyl-2,3-dihydrofuran was hydrogenated following the usual procedure (40 psig using supported palladium catalyst). After distillation, the hydrogenated mixture contained 88.7 weight percent 4-carbethoxy-2-ethyl-2,5-dimethyl-2,3-dihydrofuran and 9.4 weight percent 4-carbethoxy-2-isopropyl-5-methyl-2,3-dihydrofuran. The odor of the hydrogenated material was much improved over that of the unhydrogenated mixture. Whereas the unsaturated mixed product was somewhat floral (jasmine) and lactonic in character, a pronounced weedy character predominated. Upon hydrogenation, however, the sweet, fruity, floral, lactonic notes were enhanced and predominated. The lactonic character was reminiscent of coconut, jasmine, and gardenia and the fruitiness was reminiscent of grape. The overall floral impact was very natural.

By short path distillation of a portion of the hydrogenated mixture, essentially pure 4-carbethoxy-2-ethyl-2,5-dimethyl-2,3-dihydrofuran (B.P. 90° C. @ 11 mm Hg; $n_D^{25°}$1.4639) was obtained. The very natural floral lactonic notes were even more evident with this product and were reminiscent of methyl jasmonate. The structure of the product

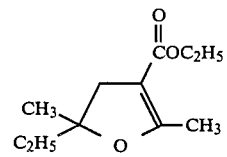

was confirmed by infrared and nuclear magnetic resonance spectroscopy.

I.R. (film): 2860–2960, 1695, 1615, 1235, 1065 cm⁻¹.

nmr (CDCl₃) δ: 1.04 (t, 3H (C(CH₃)(CH₂CH₃))), 1.38 (t, 3H (O—CH₂—CH₃)), 1.45 (s, 3H (C(CH₃)(CH₂CH₃))), 1.82 (m, 2H (C(CH₃)(CH₂CH₃)), 2.32 (t, 3H (C(O)(═C)(CH₃))), 2.84 (m, 2H (ring methylene)), 4.36 (q. 2H (O—CH₂—CH₃)).

The 4-carbethoxy-2-ethyl-2,5-dimethyl-2,3-dihydrofuran was adsorbed on a cosmetic grade talc at a 0.1 weight percent level. The talc took on a pleasing floral lactonic character. No degradation of color or odor was observed upon storage. Similarly, 0.1 weight percent of the product was adsorbed on a commercially available unfragranced detergent. The resulting fragranced detergent had a very pleasant odor characteristic of methyl jasmonate and remained free flowing with no evidence of discoloration. Fragranced soap bars having a very natural floral lactonic note were also prepared by thoroughly blending 0.5 weight percent of the 4-carbethoxy-2-ethyl-2,5-dimethyl-2,3-dihydrofuran into a cosmetic grade tallow/coconut fatty soap stock.

EXAMPLES XVI–XVIII

To demonstrate the versatility of the 2,3-dihydrofuran fragrance derivatives of the present invention, three liquid soaps were prepared in accordance with the following recipe:

|  | Parts By Weight |
| --- | --- |
| Emersal ® 6400 Sodium Lauryl Sulfate | 30.0 |
| Emid ® 6511 Lauramide DEA | 6.0 |
| Lanoquat ® 1756 Lanolin Quaternary | 1.0 |
| Emerest ® 2350 Glycol Stearate | 1.0 |
| Emersol ® 132 Stearic Acid | 0.5 |
| Triethanolamine | 0.3 |
| Emeressence ® 1160 Rose Ether ® Phenoxyethanol | 1.0 |
| Deionized Water | 60.2 |

To prepare the liquid soaps the ingredients were slowly heated to 75° C. until a homogeneous melt was obtained. The mixture was then cooled to 40° C. with agitation and 0.5 weight percent of the fragrance component added and thoroughly blended. For the product of Example XVI, 4-carbethoxy-2-ethyl-5-methyl-2,3-dihydrofuran was employed. Liquid soaps were also prepared using 4-carbomethoxy-2-ethyl-5-methyl-2,3-dihydrofuran (Ex. XVII) and 4-carbethoxy-2-ethyl-2,5-dimethyl-2,3-dihydrofuran (Ex. XVIII) as the fragrance additives. All of the resulting soap preparations had very natural floral odors and were stable pearlescent liquids. The formulations showed no evidence of discoloration or phase separation upon storage at ambient conditions. The liquid soap formulated with the 4-carbethoxy-2-ethyl-5-methyl-2,3-dihydrofuran had a natural herbal chamomile-like odor. The products of Examples XVII and XVIII had pleasing jasmonic and sassafras fragrances, respectively.

EXAMPLES XIX–XX

Mild fragranced shampoos were prepared in accordance with the following recipe:

|  | Parts by Weight |
| --- | --- |
| Emersal ® 6455 Sodium Laureth Sulfate | 20.0 |
| Emery ® 5320 Laureth Sulfosuccinate | 10.0 |
| Emid ® 6515 Cocamide DEA | 5.0 |
| Emery ® 5412 Cocoamphoglycinate | 4.0 |
| Emeressence ® 1160 Rose Ether ® Phenoxyethanol | 0.7 |
| Deionized Water | 60.3 |

To obtain the shampoo, the above ingredients were combined and heated with agitation until a homogeneous blend was obtained. Viscosity and pH were then adjusted by the addition of small increments of sodium chloride and citric acid, respectively, followed by the addition of 0.1 weight percent of the 2,3-dihydrofuran fragrance compound.

Shampoos were prepared utilizing 4-carbethoxy-2-ethyl-5-methyl-2,3-dihydrofuran (Ex. XIX), 4-carbomethoxy-2-ethyl-5-methyl-2,3-dihydrofuran (Ex. XX), and 4-carbethoxy-2-ethyl-2,5-dimethyl-2,3-dihydrofuran (Ex. XXI) as fragrance additives. All of the resulting shampoo formulations were stable, clear viscous liquids and had pleasing natural floral odors. The shampoo formulated using 4-carbethoxy-2-ethyl-5-methyl-2,3-dihydrofuran had a natural herbal chamomile-like odor. The products of Examples XX and XXI, respectively, had pleasing jasmonic and sassafras fragrances.

EXAMPLE XXII

Utilizing the oxidative addition procedure previously described, piperylene (55 mls) and ethyl acetoacetate (65 grams) were reacted. For the oxidation, manganese (III) acetate obtained by the reaction of potassium permanganate (30 grams) and manganese (II) acetate (196 grams) in 425 mls acetic acid was employed with cupric acid (1 gram) catalyst. 4-Carbethoxy-5-methyl-2-propenyl-2,3-dihydrofuran was recovered and hydrogenated in accordance with the usual procedure to obtain 4-carbethoxy-5-methyl-2-propyl-2,3-dihydrofuran. Distillation of the 4-carbethoxy-5-methyl-2-propyl-2,3-dihydrofuran using a spinning band still yielded 99+% pure product (B.P. 73° C. @ 10 mm Hg: $n_D^{27°} 1.4650$). The pure material had a very natural sweet, lactonic, coumarinic, tobacco, tonka bean-like aroma and was useful in lavender and bergamot fragrances. The structure of the product

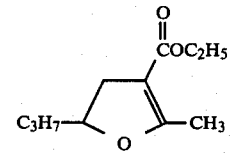

was confirmed by infrared and nuclear magnetic resonance spectroscopy.

I.R. (film): 2860–2960, 1690, 1635, 1220, 1075 cm$^{-1}$.

nmr (CDCl$_3$) δ: 0.95 (m, 3H (—CH$_2$—CH$_2$—C̲H̲$_3$)), 1.22 (t, 3H (O—CH$_2$—C̲H̲$_3$)), 1.60 (m, 4H (—C̲H̲$_2$—CH$_2$—CH$_3$)), 2.13 (t, 3H (C(O)(=C)(C̲H̲$_3$)), 2.80 (m, 2H (ring methylene)), 4.20 (q, 2H (O—C̲H̲$_2$—CH3)), 4.65 (m, 1H (ring H)).

EXAMPLE XXIII 2,5-Dimethyl-2,4-hexadiene and ethyl acetoacetate were reacted utilizing the oxidative addition procedure to obtain 4-carbethoxy-2-(2-methyl-1-propenyl)-3,3,5-trimethyl-2,3-dihydrofuran. Manganese (III) acetate obtained by the reaction potassium permanganate (19.75 grams) and manganese (II) acetate (122.5 grams) in 250 mls acetic acid was employed for the oxidation. The 2,5-dimethyl-2,4-hexadiene (27.5 gram) and ethyl acetoacetate (32.5 grams) were reacted in the presence of 0.5 grams cupric acetate catalyst. 4-Carbethoxy-2-(2-methyl-1-propenyl)-3,3,5-trimethyl-2,3-dihydrofuran was recovered (61% yield) and hydrogenated in ethanol using a supported palladium catalyst (5% Pd on carbon) to obtain 4-carbethoxy-2-(2-methylpropyl)-3,3,5-trimethyl-2,3-dihydrofuran. Essentially pure (97+%) 4-carbethoxy-2-(2-methylpropyl)-3,3,5-trimethyl-2,3-dihydrofuran (B.P. 136° C. @ 9.2 mm Hg: n$_D^{23°}$1.4642) was obtained upon distillation of the crude product. The product had a green vegetable odor. The structure of the product

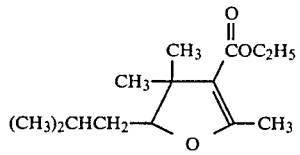

was confirmed by infrared and nuclear magnetic resonance.

I.R. (film): 2860–2960, 1692, 1623, 1195, 1070 cm$^{-1}$.

nmr (CDCl$_3$) δ: 1.00 (s, 6H (—C(C)(C)(CH$_3$) 1.25 (m, 6H (—CH—(CH$_3$)$_2$)), 1.25 (m, 1H (—CH—(CH$_3$)$_2$)), 2.10 (s, 3H (C(O)(=C)CH$_3$)), 4.20 (q, 2H (—O—CH$_2$—CH$_3$)), 4.20 (m, 1H (ring H)).

We claim:

1. 4-Carbethoxy-2-ethyl-5-methyl-2,3-dihydrofuran.
2. 4-Carbomethoxy-2-ethyl-5-methyl-2,3-dihydrofuran.
3. 4-Carbethoxy-2-ethyl-2,5-dimethyl-2,3-dihydrofuran.
4. 4-Carbomethoxy-2-ethyl-2,5-dimethyl-2,3-dihydrofuran.
5. 4-Carboethoxy-5-methyl-2-propyl-2,3-dihydrofuran.
6. 4-Carbomethoxy-5-methyl-2-propyl-2,3-dihydrofuran.
7. 4-Carbethoxy-2-(2-methylpropyl)-3,3,5-trimethyl-2,3-dihydrofuran.
8. 4-Carbomethoxy-2-(2-methylpropyl)-3,3,5-trimethyl-2,3-dihydrofuran.

* * * * *